US008380320B2

(12) United States Patent
Spital

(10) Patent No.: US 8,380,320 B2
(45) Date of Patent: Feb. 19, 2013

(54) IMPLANTABLE MEDICAL DEVICE COMMUNICATION SYSTEM WITH MACRO AND MICRO SAMPLING INTERVALS

(75) Inventor: Glenn O. Spital, Granada Hills, CA (US)

(73) Assignee: Medtronic, Inc., Minneapolis, MN (US)

( * ) Notice: Subject to any disclaimer, the term of this patent is extended or adjusted under 35 U.S.C. 154(b) by 951 days.

(21) Appl. No.: 11/224,594

(22) Filed: Sep. 12, 2005

(65) Prior Publication Data

US 2007/0060977 A1    Mar. 15, 2007

(51) Int. Cl.
*A61N 1/08* (2006.01)
(52) U.S. Cl. .......................................... 607/60
(58) Field of Classification Search .......... 607/16, 607/31–32, 60; 128/903
See application file for complete search history.

(56) References Cited

U.S. PATENT DOCUMENTS

| 4,276,618 A | 6/1981 | Green |
| 4,786,903 A | 11/1988 | Grindahl et al. |
| 4,799,059 A | 1/1989 | Grindahl et al. |
| 5,107,833 A * | 4/1992 | Barsness .................. 607/32 |
| 5,324,315 A | 6/1994 | Grevious |
| 5,342,408 A * | 8/1994 | deCoriolis et al. ............ 607/32 |
| 5,350,407 A | 9/1994 | McClure et al. |
| 5,350,411 A | 9/1994 | Ryan et al. |
| 5,549,113 A | 8/1996 | Halleck et al. |
| 5,600,707 A | 2/1997 | Miller, II |
| 5,752,977 A | 5/1998 | Grevious et al. |
| 5,843,139 A | 12/1998 | Goedeke et al. |
| 5,904,708 A * | 5/1999 | Goedeke .................. 607/18 |
| 5,995,874 A | 11/1999 | Borza |
| 6,219,580 B1 | 4/2001 | Faltys et al. |
| 6,223,083 B1 | 4/2001 | Rosar |
| 6,335,953 B1 | 1/2002 | Sanderford, Jr. et al. |
| 6,381,492 B1 | 4/2002 | Rockwell et al. |
| 6,443,891 B1 | 9/2002 | Grevious |
| 6,631,296 B1 | 10/2003 | Parramon et al. |
| 6,644,321 B1 | 11/2003 | Behm |
| 6,687,543 B1 | 2/2004 | Isaac et al. |
| 6,704,602 B2 | 3/2004 | Berg et al. |
| 6,738,670 B1 | 5/2004 | Almendinger et al. |
| 6,829,493 B1 | 12/2004 | Hunzinger |
| 6,897,788 B2 | 5/2005 | Khair et al. |
| 6,993,393 B2 | 1/2006 | Von Arx et al. |
| 2001/0012955 A1 | 8/2001 | Goedeke et al. |
| 2002/0014372 A1 | 2/2002 | Edlund |
| 2002/0026224 A1 | 2/2002 | Thompson et al. |
| 2002/0103514 A1 | 8/2002 | Abrahamson |
| 2002/0123672 A1 | 9/2002 | Christophersom et al. |

(Continued)

FOREIGN PATENT DOCUMENTS

EP    0717510 A2    6/1996
EP    1264614    12/2002

(Continued)

*Primary Examiner* — Rex R Holmes
(74) *Attorney, Agent, or Firm* — Stephen W. Bauer; Michael J. Ostrom

(57) ABSTRACT

A communication signal is communicated between an implantable medical device including an implant transceiver and an external unit including an external unit transceiver. At least one of the transceivers includes a receiver capable of sampling a communication channel for the communication signal at times based on a macro sampling interval and a micro sampling interval. The sampling includes a series of micro samples. The duration of the series of micro samples is less than the macro sampling interval.

24 Claims, 7 Drawing Sheets

U.S. PATENT DOCUMENTS

| | | |
|---|---|---|
| 2002/0183806 A1 | 12/2002 | Abrahamson et al. |
| 2003/0069614 A1* | 4/2003 | Bowman et al. ............... 607/60 |
| 2003/0097157 A1 | 5/2003 | Wohlgemuth et al. |
| 2003/0114898 A1 | 6/2003 | Von Arx et al. |
| 2003/0187484 A1 | 10/2003 | Davis et al. |
| 2003/0229383 A1* | 12/2003 | Whitehurst et al. ............ 607/60 |
| 2004/0127959 A1 | 7/2004 | Amundson et al. |
| 2004/0167587 A1 | 8/2004 | Thompson |
| 2004/0172104 A1 | 9/2004 | Berg et al. |
| 2004/0176811 A1 | 9/2004 | Von Arx et al. |
| 2004/0176822 A1 | 9/2004 | Thompson et al. |
| 2005/0249236 A1 | 11/2005 | Walden |
| 2006/0097157 A1 | 5/2006 | Ouyang et al. |
| 2007/0049983 A1 | 3/2007 | Freeberg |

FOREIGN PATENT DOCUMENTS

| | | |
|---|---|---|
| EP | 1495783 | 1/2005 |
| JP | 10256928 | 9/1998 |
| JP | 2004080704 | 7/2004 |
| WO | 9725100 | 7/1997 |
| WO | 0031998 | 6/2000 |
| WO | 0224064 | 3/2002 |
| WO | 03095024 | 11/2003 |

* cited by examiner

IMPLANTABLE MEDICAL DEVICE COMMUNICATION SYSTEM WITH MACRO AND MICRO SAMPLING INTERVALS

CROSS-REFERENCE TO RELATED APPLICATION(S)

Reference is made to the following applications, filed concurrently herewith: U.S. patent application Ser. No. 11/224,593, which granted as U.S. Pat. No. 8,065,018, entitled "SYSTEM AND METHOD FOR UNSCHEDULED WIRELESS COMMUNICATION WITH A MEDICAL DEVICE," by Gregory J. Haubrich, Len D. Twetan; David Peichel; Charles H. Dudding; George C. Rosar; and Quentin S. Denzene, U.S. patent application Ser. No. 11/224,591, which granted as U.S. Pat. No. 7,890,181, entitled "SYSTEM AND METHOD FOR UNSCHEDULED WIRELESS COMMUNICATION WITH A MEDICAL DEVICE," by Quentin S. Denzene and George C. Rosar, and U.S. patent application Ser. No. 11/224,595, entitled COMMUNICATION SYSTEM AND METHOD WITH PREAMBLE ENCODING FOR AN IMPLANTABLE MEDICAL DEVICE," by Gregory J. Haubrich, Javaid Masoud, George C. Rosar, Glenn Spital, Quentin S. Denzene, incorporated herein by reference in their entireties.

FIELD OF THE INVENTION

The present invention relates implantable medical devices, and more particularly, to wireless communication with implantable medical devices.

BACKGROUND OF THE INVENTION

Implantable medical devices (IMDs) provide therapies and monitor a wide variety of physiological events. With the increased uses of IMDs has also come the need for improved methods of communicating with and between IMDs.

Conventionally, communication with IMDs has been with magnetic field communication systems. Such systems, however, are generally only capable of communicating over very short distances, on the order of a few inches. As a result, a magnetic head of a programmer (or other external device) needs to be placed near to the IMD for communication to occur. More recently, radio frequency (RF) based communication systems have been developed for use with IMDs. RF communication provides a number of benefits over magnetic field communication systems, including much greater communication distances. However, conventional RF communication systems consume more battery power than magnetic field communication systems, thus impacting the service life of the IMD battery.

Accordingly, there is a need to improve RF receiver efficiency and inter-IMD communication modalities to conserve battery life.

RF communication may generally be divided into two categories: synchronous and asynchronous. Synchronous communication is conducted at scheduled times. However, in synchronous communication systems, the internal clocks of two communicating devices are prone to drift over time. As more time elapses, the internal clocks become increasingly out of sync, such that neither device can precisely detect when the other device will commence communication. To compensate for this drift, one or both of the devices must stay in an "on" mode. During that time, energy is consumed while no communication is effected.

In an asynchronous communication system, transmission occurs at random times. Because it is impractical to maintain the receiver on at all times, asynchronous communication systems utilize sampling methods in which the receiver is repeatedly turned on for brief periods to check for a transmission signal and turned on fully when the signal is detected. The more often the receiver is turned on, the faster the response time of the receiver. However, more energy is required. To guarantee that data will be received, the transmitter transmits a preamble for at least as long as the time interval between samples prior to transmitting a message. Once the preamble is detected, the receiver remains on until the message is received. As a result, energy is consumed by the receiver while receiving the preamble, a time in which no valuable communication is taking place.

DETAILED DESCRIPTION

According to an embodiment of the present invention, a communication system includes an implantable medical device having a first transceiver and an external unit including a second transceiver. At least one of the transceivers includes a receiver configured to sample a communication channel based on a macro sampling interval and a micro sampling interval. The duration of a series of micro samples is spaced by the micro sampling interval and is set to be smaller than the macro sampling interval.

Figure 1:
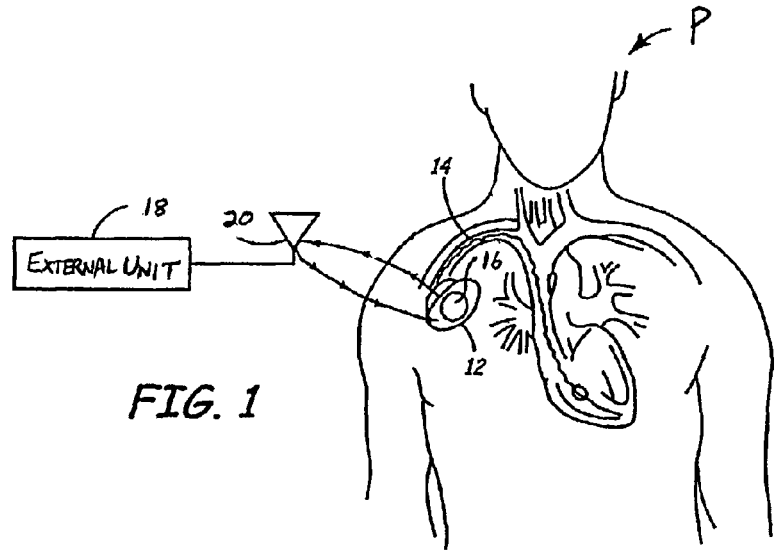
FIG. 1 is a schematic diagram illustrating bi-directional RF communication between an implantable medical device (IMD) and an external unit.

FIG. 1 is a schematic diagram illustrating communication system 10 for communication between IMD 12, which includes lead 14 and antenna 16, and external unit 18. In one embodiment, IMD 12 is an implantable cardioverter defibrillator (ICD). However, the present invention is broadly applicable to many types of medical devices, including implantable and externally mounted medical devices. IMD 12 includes features to sense, detect, and monitor cardiac signals from patient P and delivers them as needed. Lead 14 is implanted to transfer information as well as provide therapy to specific chambers of the heart. Antenna 16 is used to communicate with external unit 18 and may be any device capable of sending or receiving electromagnetic waves, including for example a surface mounted antenna, an inductor, or a half-wave strip.

External unit 18 is a device, such as a programmer, capable of bi-directional communication with IMD 12 via antenna 20.

External unit 18 includes antenna 20, which may be any type of RF antenna capable of communicating in the desired RF frequencies with IMD 12, and may be located inside or outside of a housing of external unit 18.

Figure 2:
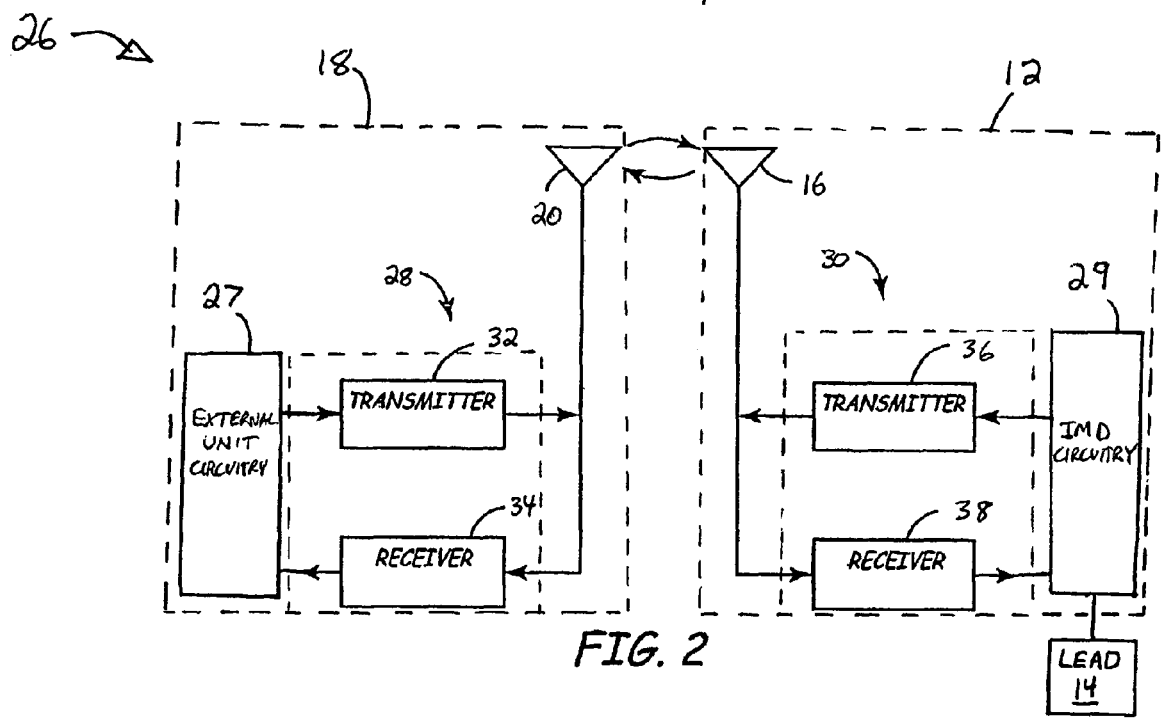
FIG. 2 is a block diagram illustrating the components of an IMD and the external unit that make up an RF communication system.

FIG. 2 is a block diagram illustrating some of the functional components of IMD 12 and external unit 18 that make up communication system 10. External unit 18 includes antenna 20, circuit 27, and transceiver 28. Antenna 20 is coupled to transceiver 28. Circuit 27 includes a microcomputer and that controls the operation of external unit 18. Transceiver 28 allows external unit circuitry 27 to transmit and receive communications with IMD 12. Transceiver 28 includes transmitter 32 and receiver 34, which are coupled to antenna 20.

IMD 12 includes antenna 16, IMD circuitry 29, and transceiver 30 (which includes transmitter 36 and receiver 38). IMD circuitry 29 includes a microprocessor for controlling the operation of IMD 12 and for processing medical data, therapy delivery circuitry for delivering a therapy through lead 14, and sensors for generating medical data relating to patient P (including data generated by detecting electrical signals on lead 14). Transceiver 30, and antenna 16 enable IMD circuitry 29 to transmit and receive communications with external unit 18.

Communication between IMD 12 and external unit 18 can be performed over any communication band, such as a public radio frequency band, or the Medical Implant Communication (MICs) band between 402 MHz and 405 MHz. Although the present invention is described with reference to radio frequency bands, it is recognized that the present invention is also beneficial with other types of electromagnetic communication.

Because IMD 12 has a finite battery capacity, an important consideration in the design of RF communication system 26 is the energy efficiency of IMD 12. A substantial factor in the energy efficiency of IMD 12 is the time transceiver 30 spends either transmitting or receiving. By decreasing the total on-time of transceiver 30, the energy efficiency of transceiver 30 is improved, leading to increased battery life of IMD 12. Energy efficiency is less of an issue in the design of transceiver 28 of external unit 18, because external unit 18 is generally connected to an external power source such as a 120V AC. Therefore, methods of operating transceivers 28 and 30 that reduce the energy consumption of transceiver 30, even in exchange for additional energy consumption of transceiver 28, are beneficial.

While transmitters only need to be turned on when there is something to transmit, receivers must be turned on much more frequently. No communication can take place unless the receiver is on, at least momentarily, to detect an attempted transmission. To provide a fast response time, a receiver may sample a communication channel as often as twice every second or more. A receiver that turns on twice every second will turn on 172,800 times in one day. A transmitter, on the other hand, may turn on only a handful of times in that same period. Therefore, increased energy efficiency of a receiver can provide a substantial increase in the effective life of the device.

The present invention utilizes macro and micro sampling intervals to improve the energy efficiency of the transceivers of a communication system. Two examples will now be described with reference to FIGS. 3-5 and 6-8 respectively. In the first example, transmitter 32 of external unit 18 transmits to receiver 38 of IMD 12. Receiver 38 operates by sampling at macro sampling intervals to detect a preamble segment 42, followed by sampling at micro sampling intervals to detect attention segment 44, and thereafter receive data 48. This reduces the energy consumed by receiver 38 of IMD 12. The second example reverses the roles such that transmitter 36 of IMD 12 transmits to receiver 34 of external unit 18. Receiver 34 operates by calculating a drift window surrounding a scheduled time slot. Scheduled time slots are spaced by the macro sampling interval. Receiver 38 samples at each micro sampling interval within the drift window until it detects attention segment 94 and thereafter receives data 98.

Sampling based on macro sampling intervals and micro sampling intervals decreases the total on-time of receiver 34 or 38 and correspondingly reduces the total energy consumed. The energy savings are realized as a result of receiver 34 or 38 being turned off between samples, rather than staying on during each of the sampling intervals.

Figure 3:
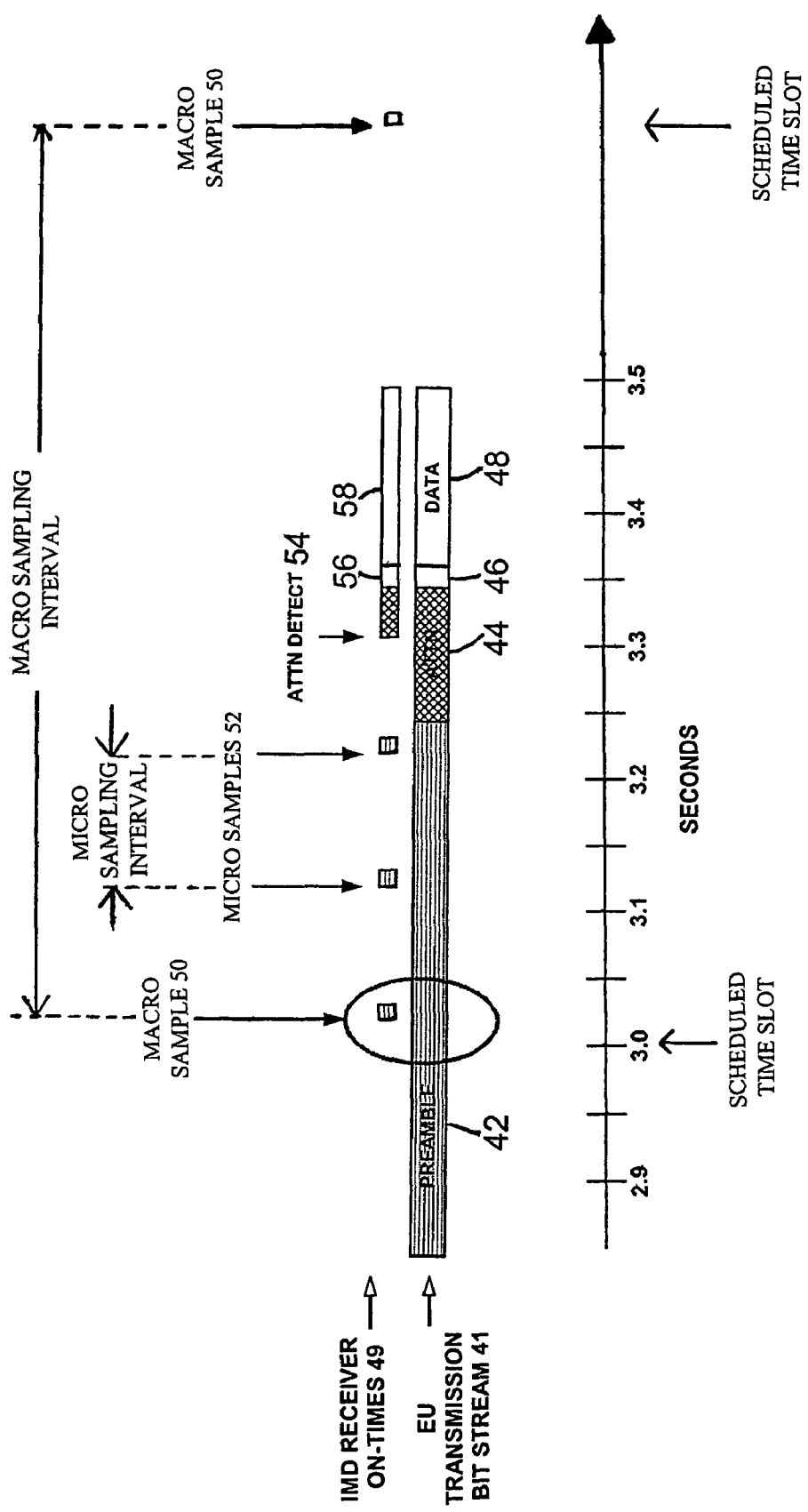
FIG. 3 is a time line illustrating a transmission bit stream from a transmitter of the external unit and receiver on-times of the IMD.
Figure 4:
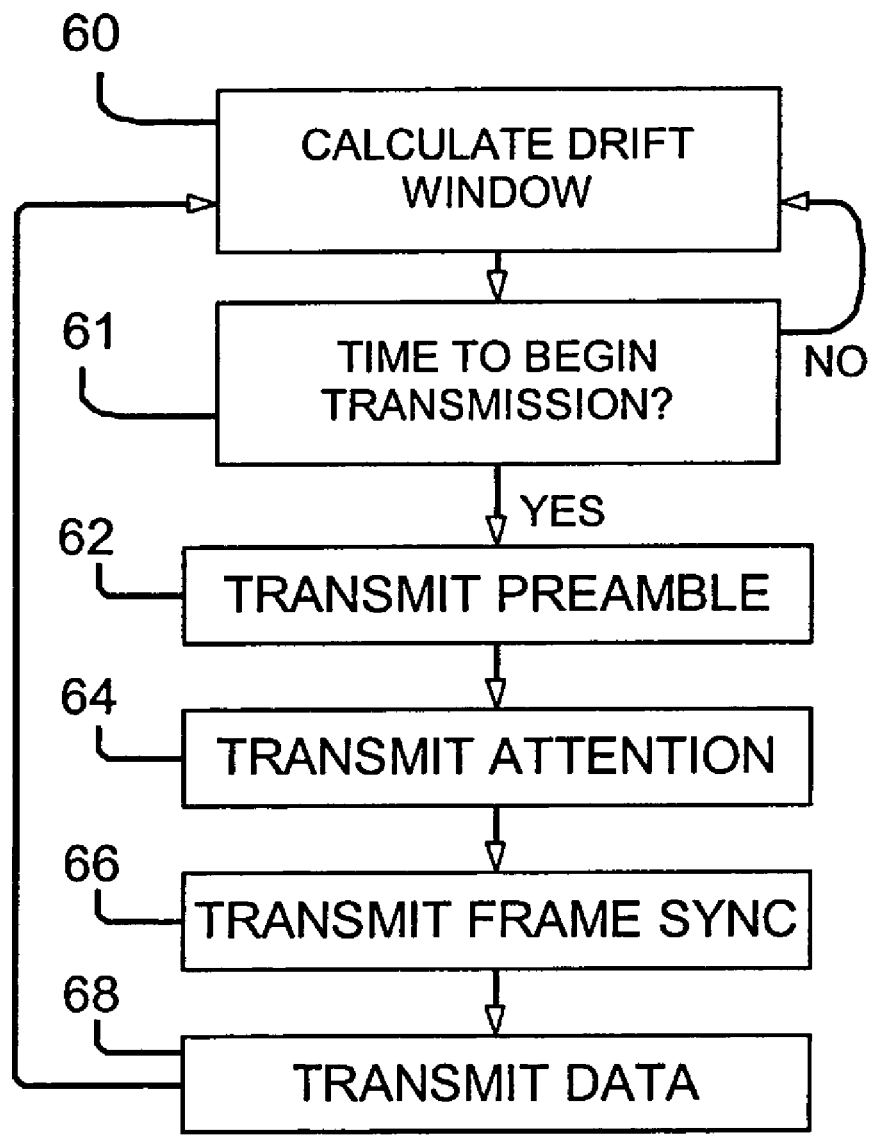
FIG. 4 is a flow chart illustrating one embodiment of a method of operating the transmitter of the external unit.
Figure 5:
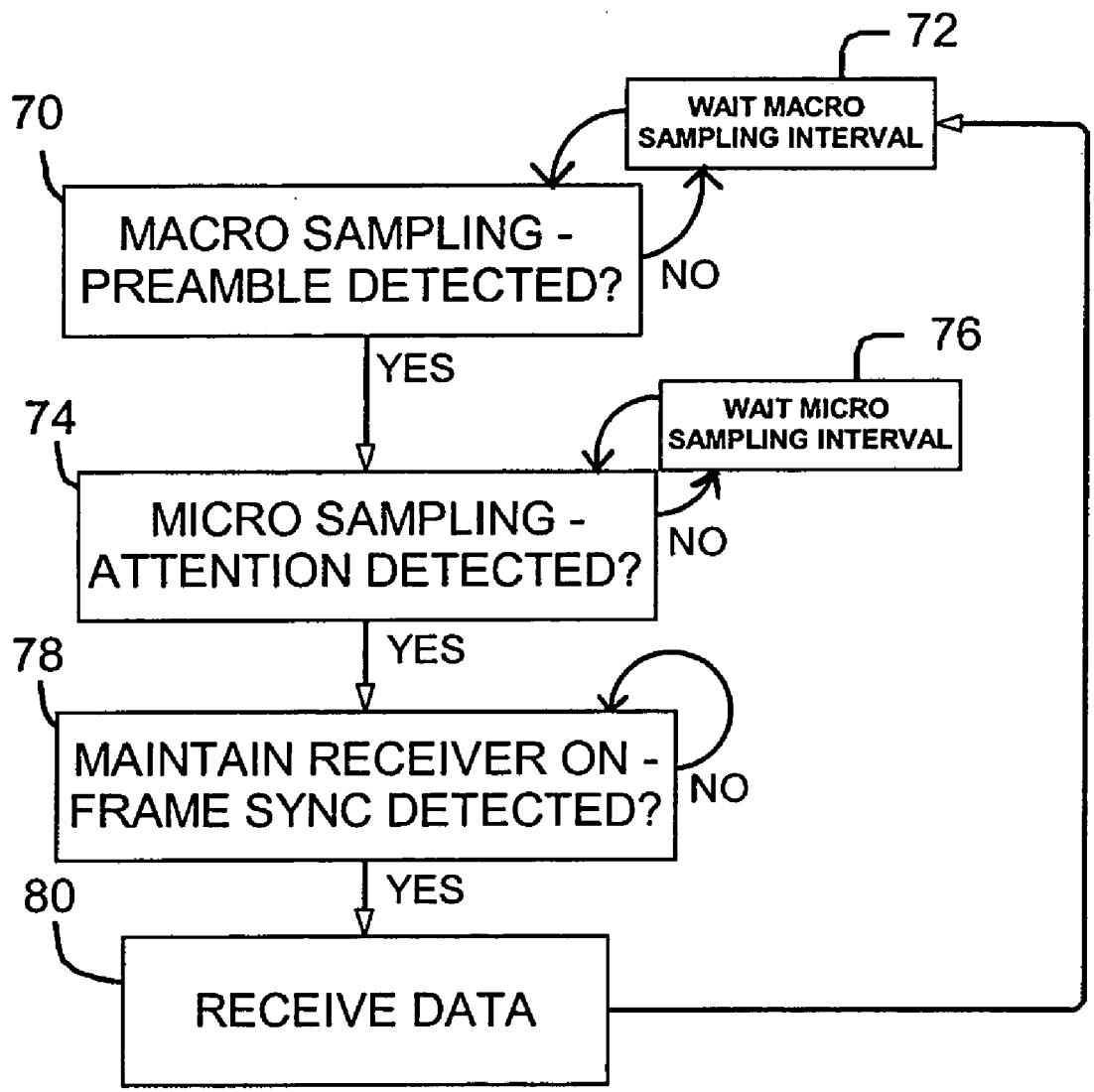
FIG. 5 is a flow chart illustrating one embodiment of the method of operating the receiver of the IMD.

FIGS. 3-5 illustrate a method for transmitting data from external unit 18 to IMD 12. FIG. 3 is a timeline illustrating transmission bit stream 41 from external unit transmitter 32 and receiver on-times 49 of IMD receiver 38. Transmission bit stream 41 includes preamble segment 42, attention (ATTN) segment 44, frame sync segment 46, and data 48.

Preamble segment 42 is a portion of transmission bit stream 41 having a recognizable pattern. Attention segment 44 is a transmission bit stream also having a recognizable pattern, but one that is distinct from preamble segment 42. Frame sync segment 46 is a brief pattern of bits that immediately precedes data 48 and is distinguishable from attention segment 44 and data 48. Data 48 follows frame sync segment 46 and includes whatever data is to be transmitted from external unit 18 to IMD 12.

For example, preamble segment 42 may be a transmission of alternating on-off keyed (OOK) 0 and 1 bits, each having a duration of about 50 microseconds, resulting in an about 10 kHz transmission. Attention segment 44 may be a transmission of alternating OOK 1 and 0 bits, each having a duration of 50 microseconds. This transmission is equivalent to preamble segment 42 with a 180 degree phase shift. In one embodiment, frame sync segment 46 is an OOK transmission of eight 1 bits. A pattern of a known length, such as eight bits is beneficial to ensure that frame sync segment 46 is not confused with data 48.

IMD receiver on-times 49 are also illustrated in FIG. 3, which include macro samples 50, micro samples 52, attention detect period 54, frame sync detect period 56, and receive data period 58. Receiver on-times 49 are periods in which receiver 38 is turned on either to sample for or receive transmission bit stream 41. Between receiver on-times 49, receiver 38 is turned off to conserve energy. Receiver on-times 49 will be described in further detail below with reference to FIGS. 4 and 5.

FIG. 4 is a flow chart illustrating one embodiment of a method of operating transmitter 32 of external unit 18. The method includes calculating a drift window (step 60), waiting until time to begin transmission (step 61), transmitting preamble segment (step 62), transmitting attention segment (step 64), transmitting frame sync segment (step 66), and transmitting data (step 68). In this embodiment, transmitter 32 operates in a synchronous communication mode in which both IMD 12 and external unit 18 both recognize a scheduled time slot for communication. However, over time the internal clocks may slowly drift away from each other, such that the exact scheduled time slot is no longer equivalent between the two devices.

To account for the possible drift between IMD 12 and external unit 18, transmitter 32 calculates a drift window (step 60). The deviation between the scheduled time slot according to the external unit's clock, and the scheduled time slot according to the clock of IMD 12 gives rise to the concept of a drift window. The drift window is the time interval, according to one device's clock, that encompasses the potential deviation in the scheduled time slots according to the other device's clock.

For example, if the maximum drift is known to be 100 parts per million (ppm), and it has been one hour since the last communication, the drift window is calculated by transmitter 32 to be about 0.36 seconds. ((3600 seconds/hour)×(100/1,000,000)=0.36 seconds/hour.) With the drift window known, transmitter 32 can determine the earliest time in which receiver 38 would expect communication to begin, and begin communication at that time (step 61). Specifically, the time to begin communication is calculated by transmitter 32 as the scheduled time slot (according to the external unit clock), minus ½ of the drift window period.

When it is time to transmit (step 61), transmitter 32 transmits preamble segment 42 (step 62). Preamble segment 42 informs receiver 38 that transmitter 32 has begun the transmission process. In one embodiment, preamble segment 42 is transmitted for a period equal to or greater than the length of the drift window. By transmitting preamble segment 42 for a period at least as long as the drift window, transmitter 32 ensures that receiver 38 will turn on and begin receiving at some time during preamble segment 42.

After preamble segment 42 has been transmitted (step 62), transmitter 32 transmits attention segment 44 (step 64). Attention segment 44 informs receiver 38 that data transmission is about to begin. In one embodiment, attention segment 44 is transmitted for a period of at least the micro sampling interval of receiver 38. The micro sampling interval is the period of time between consecutive micro samples 52. The micro sampling interval, for example, is 0.1 seconds. By transmitting attention segment 44 for a duration equal to or greater than, the micro sampling interval of receiver 38, transmitter 32 ensures that receiver 38 will turn on during, and receive a portion of, attention segment 44.

After attention segment 44 has been transmitted (step 64), frame sync segment 46 is transmitted (step 66). Frame sync segment 46 informs receiver 38 that data transmission immediately follows, and serves to allow receiver 48 to determine exactly when data begins. In one embodiment, frame sync segment 46 consists of a fixed length. In this way receiver 38 can distinguish between frame sync segment 46 and data 48 even if the pattern in data 48 continues the same pattern of frame sync segment 46. Immediately following the transmission of frame sync segment 46 (step 66), data 48 is transmitted (step 68), which includes whatever data is to be transmitted from external unit 18 to IMD 12, such as instructions, requests for information, pure data, transmitter ID, intended receiver ID, packet size, cyclic redundancy code (CRC), or any other desired codes or information. Data 48 can also be encrypted for greater security. At the end of data 48, an end of transmission code may also be included that informs receiver 38 that the transmission of data (step 68) is complete. Following the transmission of data 48 (step 68), transmitter 32 waits until the next scheduled communication time (steps 60 and 61).

Because transmitter 32 knows the transmission time of preamble segment 42, attention segment 44, frame sync segment 46, and data 48, transmitter 32 also knows exactly how long the total transmission will take. Transmitter 32 can provide this information to a user who initiated the telemetry transaction between external unit 18 and IMD 12 to inform the user of the status of the communication.

FIG. 5 is a flow chart illustrating operation of receiver 38 of IMD 12. The method includes macro sampling to detect preamble segment 42 (step 70) at macro sampling interval (step 72), micro sampling to detect attention segment 44 (step 74) at micro sampling intervals (step 76) until attention segment 44 is detected, maintaining receiver 38 on until detection of frame sync segment 46 (step 78), and receiving data 48 (step 80).

Receiver 38 begins by macro sampling for preamble segment 42 at the scheduled time slot (step 70). Between each macro sample, if preamble segment 42 is not detected, receiver 38 turns off for a macro sampling interval (step 72), which is equal to the time between scheduled communication time slots. It is beneficial for receiver 38 to sample for only a short duration to conserve energy. In one embodiment, receiver 32 is turned on for 2 milliseconds per sample. If receiver 38 detects preamble segment 42 while macro sampling, receiver 38 knows that transmitter 32 has begun the transmission of transmission bit stream 41.

After receiver 38 has detected preamble segment 70, the process of micro sampling to detect attention segment 42 begins (step 74). Receiver 38 turns off between consecutive micro samples for a micro sampling interval (step 76) to further conserve energy. As the names suggest, the micro sampling interval is less than the macro sampling interval. Furthermore, the duration of a series of micro samples is also less than the macro sampling interval. During each micro sample, receiver 38 verifies that transmission bit stream 41 is still present, and also monitors for attention segment 44 to begin.

By turning off receiver 38 between micro samples, considerable energy savings can be realized. For example, 98% of the energy is conserved between macro sample 50 and detection of attention segment 54, if each micro sample 52 lasts for 2 milliseconds, and the micro sampling interval is 0.1 seconds, as compared to maintaining receiver 38 on during this same period.

Micro sampling (step 74) continues until attention segment 44 is detected. At this point, receiver 38 knows that transmitter 32 is about to begin transmitting data 48. As a result, receiver 38 stays on and continues receiving the rest of attention segment 44 (Step 78) to detect frame sync segment 46. After receiving frame sync segment 46 (step 78), receiver 38 receives data 48 (step 80) that immediately follows. Receiver 38 then waits until the next scheduled time slot (step 72) to macro sample for transmission bit stream 41 (step 70).

Although the embodiment of FIGS. 3-5 has been described with reference to a synchronous communication system, it is recognized that it is equally applicable to an asynchronous communication system. In such a case, transmitter 32 does not know when receiver 38 will sample for a transmission, but it does know that it will occur within the macro sampling interval. By transmitting preamble 42 to a duration at least as long as the macro sampling interval, transmitter 32 is able to guarantee that the transmission will be received by receiver 38.

Figure 6:
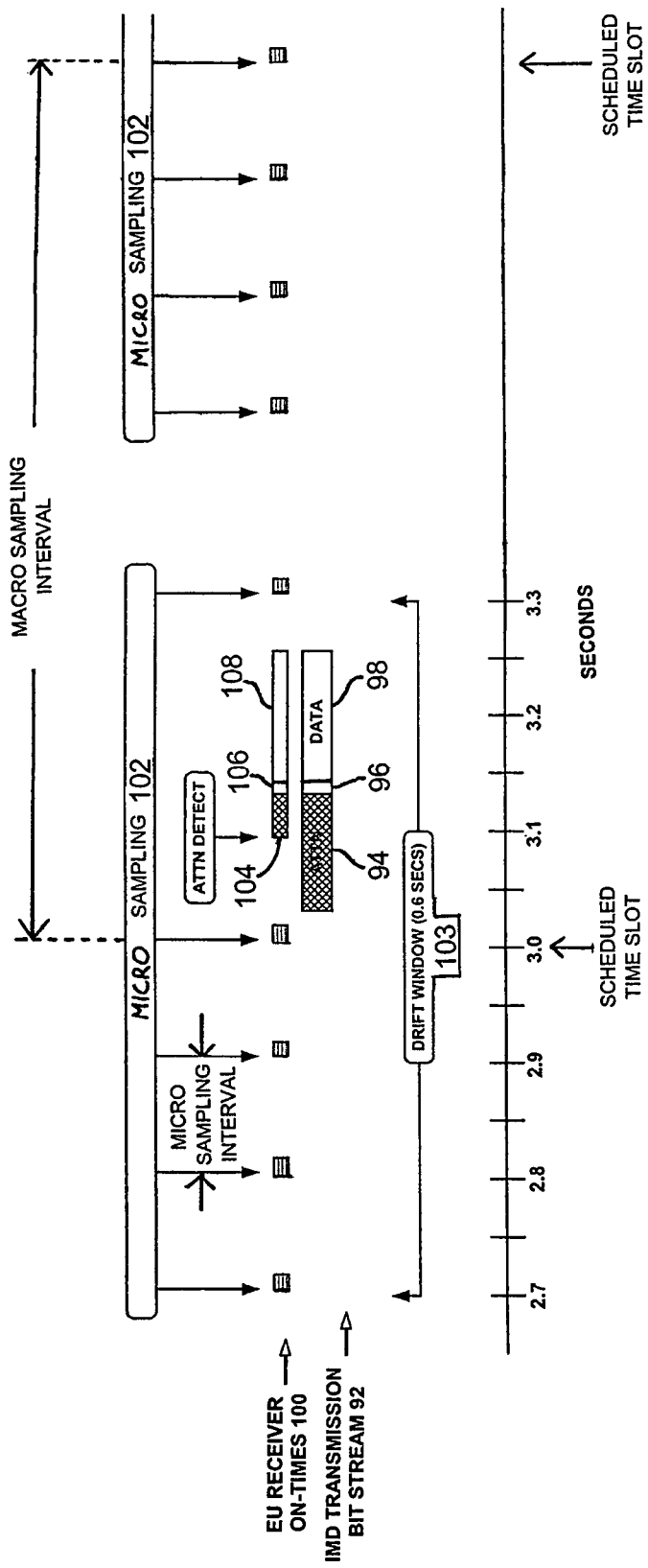
FIG. 6 is a time line illustrating a transmission bit stream from a transmitter of the IMD and receiver on-times of the external unit.
Figure 7:
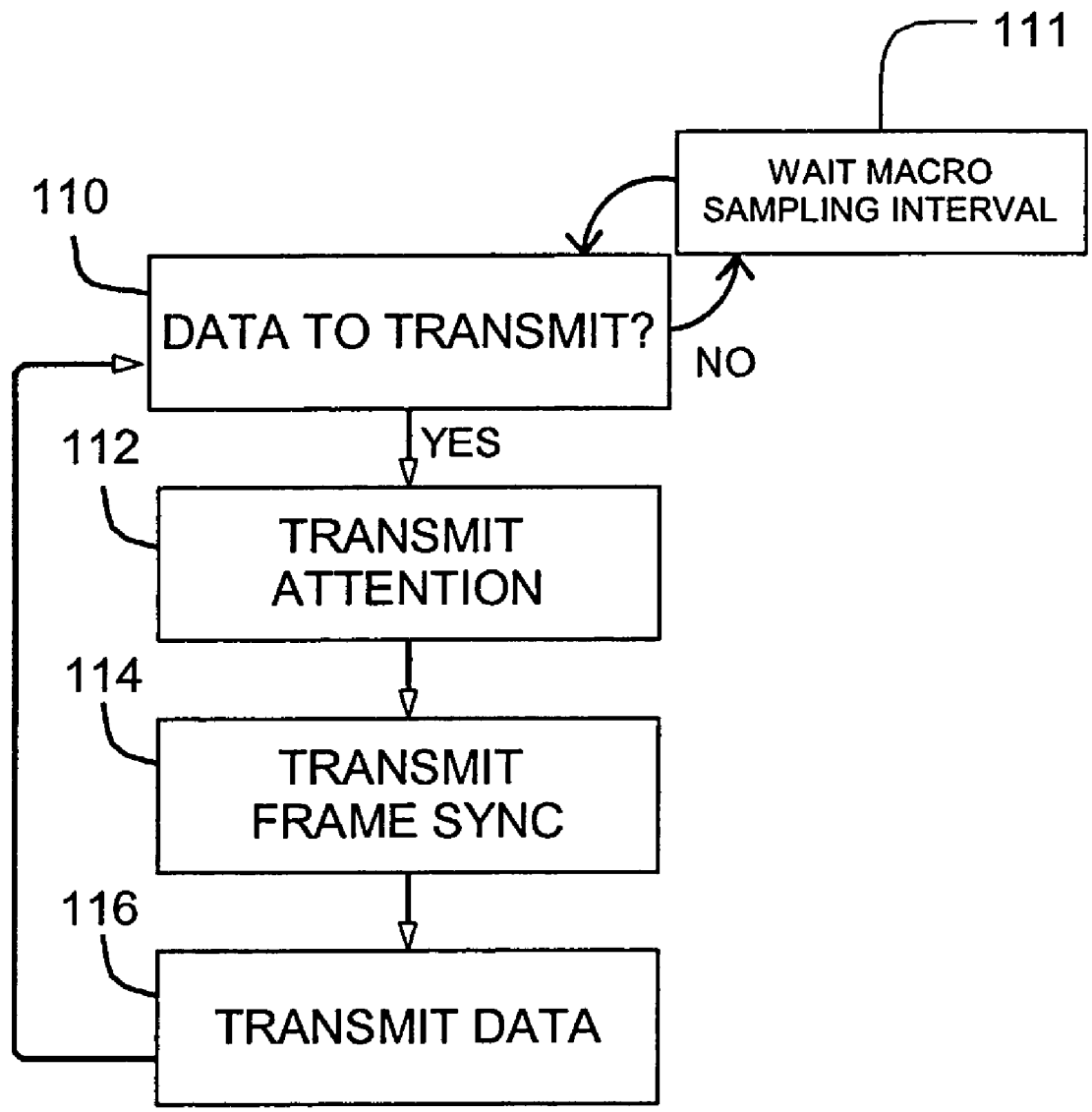
FIG. 7 is a flow chart illustrating one embodiment of a method of operating the transmitter of the IMD.
Figure 8:
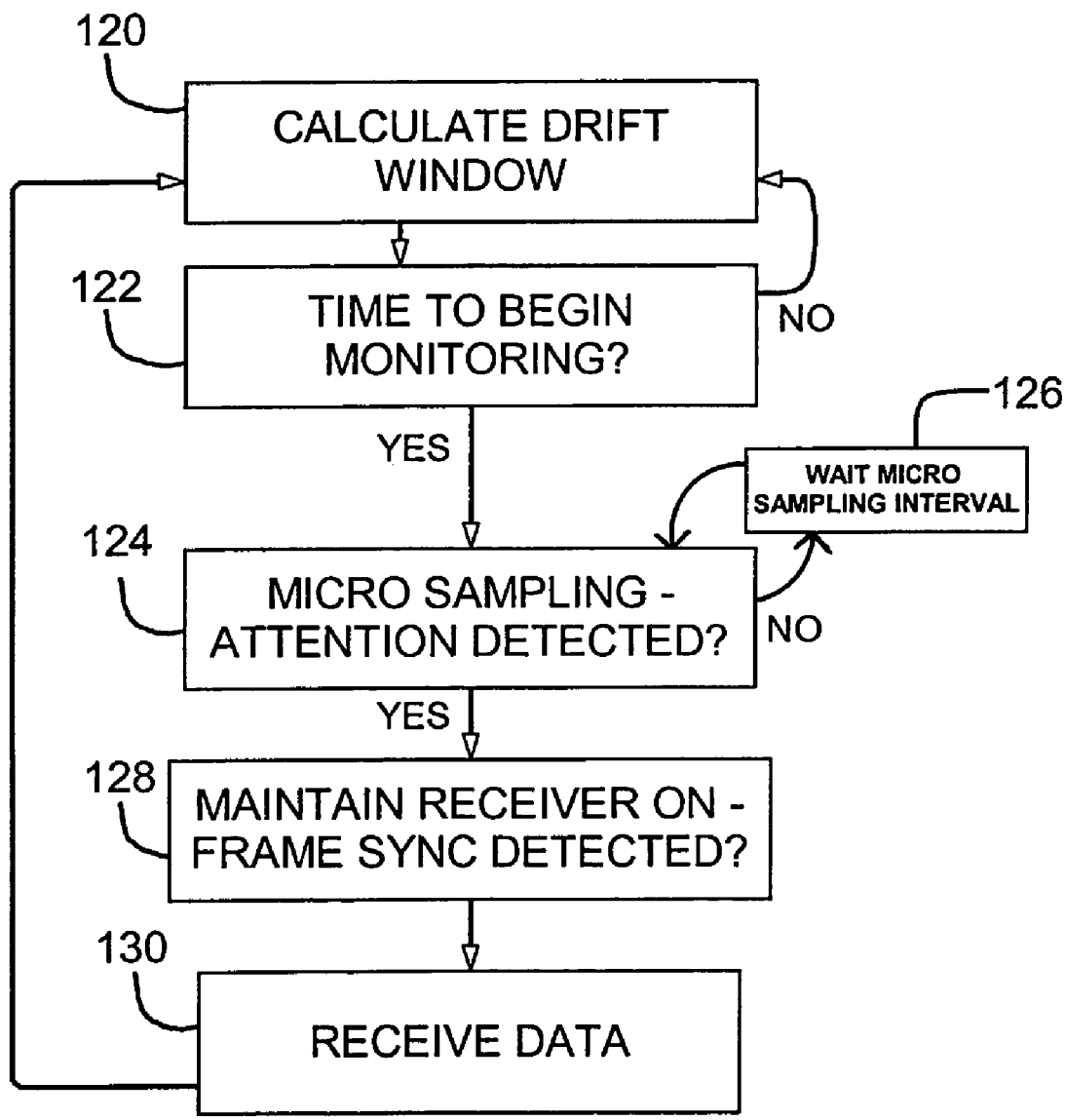
FIG. 8 is a flow chart illustrating one embodiment of a method of operating the receiver of the external unit.

FIGS. 6-8 illustrate a system and method for transmitting data from IMD 12 to external unit 18 in a synchronous communication system. The system and method reduces the energy consumed by transmitter 36 of IMD 12, and provides an energy efficient method of operating receiver 34.

FIG. 6 is a timeline illustrating transmission bit stream 92 from transmitter 36 of IMD 12 and receiver on-times 100 of receiver 34 of external unit 18. Transmission bit stream 92 includes attention segment 94, frame sync segment 96, and data 98.

Attention segment 94 is a transmission bit stream having a repeating and recognizable pattern. In one embodiment, attention segment 94 is a transmission of alternating on-off keyed (OOK) 1 and 0 bits each having a duration of 50 microseconds, resulting in a 10 kHz transmission. Any other recognizable pattern could be used.

Frame sync segment 96 is a brief pattern of bits distinguishable from attention segment 94 and data 98 that immediately precedes data 98. In one embodiment, frame sync segment 96 is an OOK transmission of eight 1 bits. Any other pattern of bits could be used, as long as receiver 34 can distinguish it from both attention segment 94 and data 98. A pattern of a known length, such as eight bits, is beneficial to ensure that frame sync segment 96 is not confused with data 98. Data 98 follows frame sync segment 96 and includes whatever data is to be transmitted from IMD 12 to external unit 18.

Receiver on-times 100, as illustrated in FIG. 6, include micro samples 102, attention detect period 104, frame sync detect period 106, and receive data period 108. Receiver on-times 100 are periods when receiver 34 is turned on to sample for or receive transmission bit stream 92. Between receiver on-times 100, receiver 34 is turned off to conserve energy. Receiver on-times 100 will be described in further detail below with reference to FIGS. 7 and 8.

FIG. 7 is a flow chart illustrating one embodiment of a method of operating transmitter 36 of IMD 18. The method includes waiting for data to transmit (step 110) at a scheduled time that occurs at the macro sampling internal (step 111), transmitting attention segment (step 112), transmitting frame sync segment (step 114), and transmitting data (step 116). To conserve energy within IMD 12, transmitter 36 is preferably kept off as much as possible.

If there is data that needs to be transmitted, transmitter 36 begins transmission bit stream 92 at a time in which IMD 12 and external unit 18 have a scheduled communication session time slot. If data is available to transmit (step 110) at the macro sampling interval (step 111), transmitter 36 transmits attention segment 94 (step 112) with a duration that slightly exceeds the micro sampling interval. Attention segment 94 serves to inform receiver 34 that transmitter 36 is about to transmit data. As described below, receiver 34 performs a series of micro samples 102 to detect the presence of transmission bit stream 92. Each micro sample 102 is spaced by the micro sampling interval. In one embodiment, the micro sampling interval is 0.1 seconds. By transmitting attention segment 94 for a period equal to the micro sampling interval of receiver 34, transmitter 36 ensures that receiver 34 will turn on during, and receive a portion of, attention segment 94.

After attention segment 94 has been transmitted (step 112), frame sync segment 96 is transmitted (step 114). Frame sync segment 96 informs receiver 34 that data transmission immediately follows so that receiver 34 can determine exactly when data 98 begins. In one embodiment, frame sync segment 96 consists of a fixed length. In this way receiver 34 can distinguish between frame sync segment 96 and data 98 even if the pattern in data 98 continues the same pattern of frame sync segment 96.

Immediately following the transmission of frame sync segment 96 (step 114), data 98 is transmitted (step 116). Data 98 includes whatever data is to be transmitted from IMD 12 to external unit 18, and may include instructions, requests for information, pure data, transmitter ID, intended receiver ID, packet size, cyclic redundancy code (CRC), or any other desired codes or information. Data 98 can be encrypted for greater security. Data 98 may also include an end of transmission code that informs receiver 34 that the transmission of data (step 116) is complete. Following the transmission of data 98 (step 116), transmitter 36 waits for more data to transmit (step 110) at the next scheduled communication time (step 111).

The method of operating transmitter 36 of FIG. 7 is beneficial in reducing the energy consumed by transmitter 36 of IMD 18 by reducing the transmitter on-time needed to transmit data 98. This method also reduces the energy consumed by transmitter 36 by shifting the burden of compensating for potential drift from IMD transmitter 36 to external unit receiver 34. Rather than transmitting preamble 42 (shown in FIG. 3) throughout the drift window period, receiver 34 of external unit 18 samples periodically throughout drift window 103. Although this may slightly increase the energy consumed by receiver 34, it greatly reduces the energy consumed by transmitter 36. Because it is generally much easier to change the battery of external device 18 than the battery of IMD 12, the increased efficiency of transmitter 36 of IMD 12 is worth the slight increase in energy consumed by receiver 34 of external unit 18.

In addition, as wireless communication devices become more common, problems associated with collisions (two or more transmissions occurring at the same time on the same communication channel) also grow. Therefore, this method of operating transmitter 36 is beneficial in reducing the risk of collisions by reducing the total transmission time of transmitter 36.

FIG. 8 is a flow chart illustrating a method of operating receiver 34 of external unit 18. The method includes calculating drift window 103 (step 120), waiting for the time to begin transmission (step 122), micro sampling 102 during the drift window to detect attention segment 94 (step 124), waiting for a micro sampling interval between micro samples (step 126), maintaining receiver 34 on to detect frame sync segment 96 (step 128), and receiving data 98 (step 130).

Receiver 34 begins by calculating the drift window (step 120). The drift window calculation enables receiver 34 to know the time period in which transmission bit stream 92 could occur. Although communication is scheduled for a certain time, the actual time of communication often varies due to drift between the internal clocks of IMD 12 and external unit 18. As a result, receiver 18 is operated to monitor during drift window 103 to detect when transmitter 36 begins communication. The drift window is calculated by multiplying the time that has elapsed since the last synchronization by the maximum drift per unit of time. For example, if the maximum drift is known to be 100 ppm, and it has been one and a half hours since the last communication, the drift window would be about 0.54 seconds. ((3600 seconds/hour)×1.5 hours×(100/1,000,000)=0.54 seconds.) FIG. 6 illustrates an example of drift window 103 having a duration of about 0.6 seconds.

After calculation of the drift window (step 120), receiver 34 waits until the appropriate time to begin monitoring. In order to be sure that receiver 34 does not miss transmission bit stream 92, receiver 34 must begin monitoring at the beginning of the drift window. This beginning time is calculated by receiver 34 by subtracting ½ of the duration of the drift window, described above, from the scheduled time slot (according to the clock of receiver 34), which occurs at a macro sampling interval after the previous scheduled time slot. By beginning to monitor at this time, and continuing to monitor throughout the duration of drift window 103, receiver 34 ensures that it will be sampling at some time during attention segment 94 of transmission bit stream 92.

Once the time to begin monitoring has arrived (step 122), receiver 34 begins micro sampling to detect attention segment 94 (step 124). Receiver 34 micro samples the communication channel after each micro sampling interval of the drift window. It is beneficial to reduce the amount of on-time of micro samples 102, because the shorter they are, the less energy is used to take the sample. In one embodiment, each micro sample 102 is 2 milliseconds long. After each micro sample 102, receiver 34 turns off for a micro sampling interval (step 126), such as 0.1 seconds, until the next micro sample 102. Micro sampling intervals 126 allow receiver 34 to save additional energy while waiting for data transmission to begin.

After receiver 34 has detected attention segment 94 of transmission bit stream 92 (step 124), receiver 34 knows that transmitter 36 is about to begin transmitting data 98. As a result, receiver 34 stays on until frame sync 96 is detected (step 128).

Immediately after the reception of frame sync 96, data 98 is received by receiver 34 (step 130). Receiver 34 then waits until the next time to begin monitoring (steps 120 and 122), which occurs after about a macro sampling interval.

The method of operating receiver 34 reduces the energy consumed by transmitter 36 of IMD 12 by reducing the amount of time that transmitter 36 must be on.

Although the present invention has been described with reference to preferred embodiments, workers skilled in the art will recognize that changes may be made in form and detail without departing from the spirit and scope of the invention. In particular, the present invention has been described with reference to implantable medical devices and external units. It is recognized that in some situations it would be desirable to use the present invention for communications between implantable medical devices, between external units, among a wireless network of implantable and external devices, or to reverse the roles of the implantable medical device and the external unit.

What is claimed is:

1. A medical device comprising:
   device circuitry for controlling the operation of the medical device and for processing data;
   a receiver configured to sample at a macro sampling interval to detect presence of a first portion of a transmission signal on a communication channel that includes a first pattern of bits and, upon detecting the first portion of the transmission signal, the receiver is configured to sample at a micro sampling interval to detect presence of a second portion of the transmission signal on the communication channel that includes a second pattern of bits equivalent to the first portion of the transmission signal with a 180 degree phase shift, and thereafter receive data contained in the transmission signal,
   wherein the macro sampling interval corresponds to a time between scheduled sampling time slots configured according to an external clock and the micro sampling interval corresponds to a period of time that is smaller than the macro sampling interval such that a duration of a series of samples spaced by the micro sampling interval is less than the macro sampling interval.

2. The medical device of claim 1, wherein the first portion of the transmission signal is a preamble segment of the transmission signal having a first pattern of alternating on-off keying (OOK) 1 and 0 bits, and the second portion of the transmission signal is an attention segment of the transmission signal having a second pattern of alternating on-off keying (OOK) 1 and 0 bits equivalent to the first portion of the transmission signal with a 180 degree phase shift.

3. The medical device of claim 2, wherein the receiver remains on after detecting presence of the attention segment to receive a frame sync segment and the data.

4. The medical device of claim 2, wherein a duration of the preamble segment is greater than the macro sampling interval.

5. The medical device of claim 2, wherein a duration of the attention segment is greater than the micro sampling interval.

6. The medical device of claim 1, wherein the medical device is an implantable medical device.

7. A communication system comprising:
   an implantable medical device including an implant transceiver;
   an external unit including an external unit transceiver, wherein the transceivers of the implantable medical device and the external unit are configured to operate in a synchronous communication mode in which both transceivers recognize scheduled time slots for communication;
   wherein at least one of the transceivers includes a receiver that is configured to sample at a macro sampling interval for a first portion of a communication that includes a first pattern of bits and, upon detecting the first portion of the communication, the receiver is configured to sample at a micro sampling interval for a second portion of the communication that includes a second pattern of bits equivalent to the first portion of the transmission signal with a 180 degree phase shift, and thereafter receive data contained in the communication;
   wherein the macro sampling interval corresponds to a time between scheduled sampling time slots and the micro sampling interval corresponds to a period of time that is smaller than the macro sampling interval such that a duration of a series of samples spaced by the micro sampling interval is less than the macro sampling interval.

8. The communication system of claim 7, wherein the receiver is part of the implant transceiver.

9. The communication system of claim 8, wherein the external unit transceiver includes a transmitter capable of transmitting the communication signal including a preamble segment, an attention segment, a frame sync segment, and data; a duration of the preamble segment being at least as long as the macro sampling interval of the receiver; a duration of the attention segment being at least as long as the micro sampling interval; and wherein the data follows the frame sync segment.

10. The communication system of claim 7, wherein the receiver is part of the external unit transceiver.

11. The communication system of claim 7,
   wherein the external unit transceiver includes a receiver configured to sample for a transmission bit stream at the micro sampling interval;
   wherein the implant transceiver includes a transmitter for transmitting a bit stream including an attention segment, a frame sync segment, and data, a duration of the attention segment being at least as long as the micro sampling interval of the receiver of the external unit, and wherein the data follows the frame sync segment.

12. The communication system of claim 9, wherein the transmitter of the external unit is configured to determine a drift window representing a time interval including a potential deviation in scheduled time slots according to a clock of the implantable medical device and to transmit the preamble signal during the drift window.

13. A medical device configured to receive a transmission bit stream that includes a preamble segment, an attention segment, a frame sync segment and data, the medical device comprising:
   device circuitry configured to control the operation of the medical device and for processing data; and
   a receiver configured to sample for the preamble segment of the transmission bit stream using a macro sampling interval, to sample for the attention segment the transmission bit stream using a micro sampling interval upon detecting the preamble segment of the transmission bit stream, wherein the macro sampling interval is greater than the micro sampling interval, and to remain on to receive the frame sync segment and the data, wherein the receiver is configured to sample at the macro sampling interval to detect a preamble segment having a first pattern of bits and upon detecting the preamble segment the receiver is configured to sample at the micro sampling interval to detect an attention segment having a second pattern of bits equivalent to the first pattern of bits of the preamble segment with a 180 degree phase shift.

14. The device of claim 13, wherein the macro sampling interval comprises a time between scheduled communication time slots that are defined according to an external clock.

15. The device of claim 14, wherein sampling for a second portion of the transmission bit stream using a micro sampling interval comprises sampling between consecutive ones of the scheduled communication time slots.

16. The device of claim 13, wherein the receiver is configured to sample at the macro sampling interval to detect a preamble segment of alternating on-off keying (OOK) 1 and 0 bits and upon detecting the preamble segment the receiver is configured to sample at the micro sampling interval to detect an attention segment of alternating OOK 1 and 0 bits equivalent to the preamble segment of the transmission signal with a 180 degree phase shift.

17. The device of claim 13, wherein the frame sync segment includes a segment of a known length that is distinguishable from the attention segment and the subsequent data.

18. The device of claim 17, wherein the frame sync segment includes a series of OOK 1 or 0 bits.

19. The device of claim 13, wherein the receiver is configured to wait until a next scheduled communication time slot to sample for a preamble segment after receiving the data.

20. The device of claim 13, further comprising a transmitter that is configured to transmit a bit stream to an external unit, wherein the transmission bit stream includes a second attention segment, a second frame sync segment and second data.

21. The device of claim 20, wherein the bit stream transmitted by the transmitter does not include a preamble segment.

22. The device of claim 20, wherein the transmitter is configured to transmit the bit stream at a scheduled communication time slot.

23. The communication system of claim 11, wherein the bit stream transmitted by the transmitter of the implantable medical device does not include a segment that is longer than the macro sampling interval.

24. The communication system of claim 11, wherein the receiver of the external unit is configured to determine a drift window representing a time interval including a potential deviation in scheduled time slots according to a clock of the implantable medical device and to sample for the transmission bit stream at the micro sampling interval during the drift window.

\* \* \* \* \*